US009144412B2

(12) United States Patent
Poulo

(10) Patent No.: US 9,144,412 B2
(45) Date of Patent: Sep. 29, 2015

(54) CONTACTLESS INFORMATION TRANSFER IN CT IMAGING MODALITY

(75) Inventor: Louis R. Poulo, Andover, MA (US)

(73) Assignee: Analogic Corporation, Peabody, MA (US)

( * ) Notice: Subject to any disclaimer, the term of this patent is extended or adjusted under 35 U.S.C. 154(b) by 516 days.

(21) Appl. No.: 13/538,141

(22) Filed: Jun. 29, 2012

(65) Prior Publication Data
US 2014/0003582 A1 Jan. 2, 2014

(51) Int. Cl.
*A61B 6/03* (2006.01)
*A61B 6/00* (2006.01)

(52) U.S. Cl.
CPC .. *A61B 6/56* (2013.01); *A61B 6/032* (2013.01)

(58) Field of Classification Search
CPC .................................. A61B 6/032; A61B 6/56
USPC ........................................................... 378/15
See application file for complete search history.

(56) References Cited

U.S. PATENT DOCUMENTS

2002/0080917 A1* 6/2002 Granfors et al. ............. 378/98.8
2008/0205446 A1* 8/2008 Popescu et al. .............. 370/473

OTHER PUBLICATIONS

Shannon, Claude E., "Communication in the Presence of Noise", Proceedings of the IEEE, vol. 86, No. 2, February 1998, pp. 447-457.
Costello, et al., "Channel Coding: The Road to Channel Capacity", Proceedings of the IEEE | vol. 95, No. 6, Jun. 2007, pp. 1150-1177.

* cited by examiner

*Primary Examiner* — Glen Kao
(74) *Attorney, Agent, or Firm* — Cooper Legal Group LLC

(57) ABSTRACT

Among other things, a communication system and technique for transferring information between a stationary unit and a rotating unit of a computed tomography (CT) system is provided. A transmitter is configured to map digital data to an analog signal by selecting, from at least three signal configurations, a signal configuration associated with the digital data, and to generate an analog signal according to the selected signal configuration. A receiver of the communication system is configured to decode an analog signal by comparing characteristics of a signal sample to at least three possible signal configurations, and to identify a digital code word that corresponds to a signal configuration (of the at least three possible signal configurations) that matches characteristics of the signal sample. In this way, in a CT application, more than 1-bit of data may be communicated per analog signal, allowing more data to be communicated faster.

20 Claims, 6 Drawing Sheets

| CODE WORD | SIGNAL CONFIGURATION | |
|---|---|---|
| | PHASE | FREQUENCY |
| 0000 | 0 | 300 MHz |
| 0001 | 0 | 300.1 MHz |
| 0010 | 0 | 300.2 MHz |
| 0011 | 0 | 300.3 MHz |
| 0100 | 90 | 300 MHz |
| 0101 | 90 | 300.1 MHz |
| 0110 | 90 | 300.2 MHz |
| 0111 | 90 | 300.3 MHz |
| 1000 | 180 | 300 MHz |
| 1001 | 180 | 300.1 MHz |
| 1010 | 180 | 300.2 MHz |
| 1011 | 180 | 300.3 MHz |
| 1100 | 270 | 300 MHz |
| 1101 | 270 | 300.1 MHz |
| 1110 | 270 | 300.2 MHz |
| 1111 | 270 | 300.3 MHz |
FIG. 5
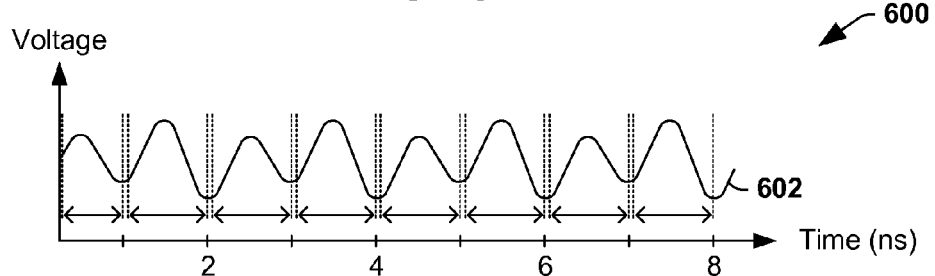
FIG. 6(a)
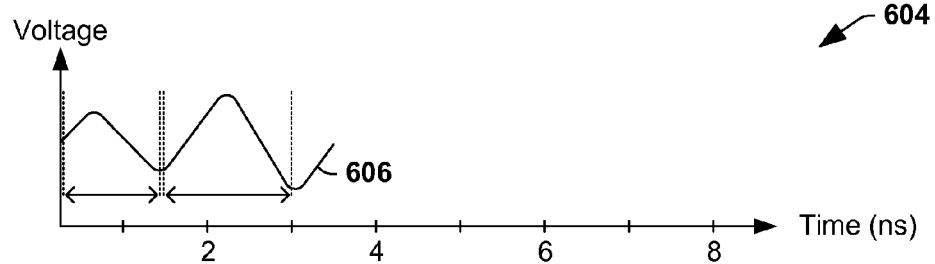
FIG. 6(b)

US 9,144,412 B2

CONTACTLESS INFORMATION TRANSFER IN CT IMAGING MODALITY

BACKGROUND

The present application relates to the transference of information across an airgap separating a receiver from a transmitter. It finds particular application in the context of computed tomography (CT) imaging modalities, which may be utilized in medical, security, and/or industrial applications, for example, where data is transferred between a rotating member and a stationary member via a contactless transfer system. However, it may also apply to other applications where data, such as image data and/or control data, for example, is wirelessly transferred between a transmitter and a receiver.

Today, CT imaging modalities (e.g., including single-photon emission computed tomography (SPECT) systems) are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

CT systems are typically configured to generate volumetric data corresponding to an object under examination. To generate this volumetric data, the CT system is generally configured to rotate a radiation source and detector array about the object under examination (e.g., causing the object to be viewed from a plurality of angles). For example, the radiation source and/or detector array may be mounted to a rotating member (at times referred to as a rotor) configured for rotation relative to a stationary member (at times referred to as a stator) configured to support the rotating member.

Given that the radiation source and detector array are mounted on the rotating member, power and/or control information (e.g., instructing the radiation source and/or other electronic components how to operate) are typically supplied to the rotating member from the stationary member. Moreover, imaging data (e.g., data generated in response to the detection of radiation by the detector array) and/or status information (e.g., regarding a status of the radiation source and/or other components attached to the rotating member) are typically transferred from the rotating member to the stationary member (e.g., for further processing and/or to be displayed to security/medical personnel). It may be appreciated that the volume of data transferred, particularly with respect imaging data, may be quite large. For example, some imaging modalities may require transfer speeds of up to 1.5 or more gigabits per second (e.g., particularly if the rotating member does not comprise a storage medium to temporarily store data until it can be transferred).

Conventionally, slip-ring assemblies have been used to transfer power and/or information (e.g., control information, status information, and/or imaging data) between the stationary member and the rotating member or more generally between a movable member and a stationary member (or between two movable members) through the physical contact of two materials (e.g., via a sliding contact). For example, a slip-ring attached to the stationary member may comprise metal brushes that are configured to physically contact electrically conductive surfaces (e.g., metal brushes) comprised on a slip-ring attached to the movable member, allowing power and/or information to be transferred between the stationary member and the movable member through one or more metal brushes.

While the use of slip-ring assemblies has proven effective for transferring power and/or information between a stationary unit and a movable unit (e.g., such as a rotating member) and/or between two movable members, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may cause interference during CT imaging. Other drawbacks of slip-ring assemblies may include cost and complexity of manufacture due to special materials and/or mechanical precision that may be required.

More recently, contactless assemblies have been devised to transfer the data between a rotating member and a stationary member. For example, U.S. Pat. No. 5,577,026 (assigned to Analogic Corporation), incorporated herein by reference, describes an approach for contactless assemblies to transfer data. While such an assembly may overcome many of the aforementioned drawbacks to a slip-ring assembly, the amount of data capable of being transferred via the foregoing contactless assemblies has been limited.

For example, such contactless assemblies implement a relatively straightforward binary signaling technique. That is, data is converted into an analog domain, with respective signals (or samples) corresponding to one of two possible binary values (e.g., a first value corresponding to "0" and a second value corresponding to "1"). Stated differently, the signal that is generated may be one of two possible variations, where a first variation is indicative of a "0" value and a second variation is indicative of a "1" value (e.g., such that respective samples represent a single bit of information). While such a technique may be relatively easy to implement (e.g., resulting in minimal data processing by a transmitter and/or receiver performing the conversation), such assemblies are not easily scalable. That is, to increase data capacity or bandwidth of the contactless assembly, additional hardware must be purchased (e.g., such as a wider bandwidth data-link) and/or by incorporating multiple data-links in parallel, for example. Thus, to increase data capacity, hardware modifications may be required that add costs and/or design constraints to the imaging system.

SUMMARY

Aspects of the present application address the above matters, and others. According to one aspect, a communication system for communicating information across a contactless data-link of a computed tomography (CT) system comprising a rotating member and a stationary member is provided. The system comprises a transmitter configured map digital data indicative of at least some of the information into a first analog signal. Mapping the digital data into the first analog signal comprises selecting, from at least three possible signal configurations, a signal configuration corresponding to the digital data and generating the first analog signal according to the selected signal configuration. The system also comprises a contactless data-link comprising a rotating portion operably coupled to the rotating member of the CT system and a stationary portion operably coupled to the stationary member of the CT system. The rotating portion is separated from the stationary portion via an airgap and the contactless data-link is configured to transfer the first analog signal from the transmitter to a receiver. The system further comprises a receiver configured to process the first analog signal to estimate the digital data mapped to the first analog signal.

According to another aspect, a method for communicating information between a rotating member and a stationary member of a computed tomography (CT) system is provided. The method comprises selecting, from at least three possible signal configurations, a first signal configuration corresponding to a first digital code word indicative of at least some of the information to be transmitted between the rotating member and the stationary member. The method also comprises generating a first analog signal according to the selected first signal configuration and transmitting the first analog signal between the rotating member and the stationary member through an airgap separating the rotating member and the stationary member. The method further comprises processing the transmitted first analog signal to decode the first analog signal and estimate the first digital code word from the decoding.

According to another embodiment, a communication system for communicating information across a contactless data-link of a computed tomography (CT) system comprising a rotating member and a stationary member is provided. The system comprises a transmitter configured map digital data indicative of at least some of the information into an analog signal. The system also comprises a contactless data-link comprising a rotating portion operably coupled to the rotating member of the CT system and a stationary portion operably coupled to the stationary member of the CT system. The rotating portion is separated from the stationary portion via an airgap and the contactless data-link is configured to transfer the analog signal from the transmitter to a receiver. The system further comprises a receiver configured to process the analog signal to estimate the digital data mapped to the analog signal by comparing one or more characteristics of the analog signal to at least three possible signal configurations to determine a matching signal configuration and identifying a digital code word associated with the matching signal configuration.

Those of ordinary skill in the art may appreciate still other aspects of the present application upon reading and understanding the appended description.

FIGURES

The application is illustrated by way of example and not limitation in the figures of the accompanying drawings, in which like references indicate similar elements and in which:

FIG. 5 illustrates an example mapping scheme for mapping digital code words to respective signal configurations.

FIG. 6(a) illustrates an example plot describing the transmission of data via a convention 1-bit binary signaling technique.

FIG. 6(b) illustrates an example plot describing the transmission of data via one or more communication techniques described herein.

DESCRIPTION

Figure 1:
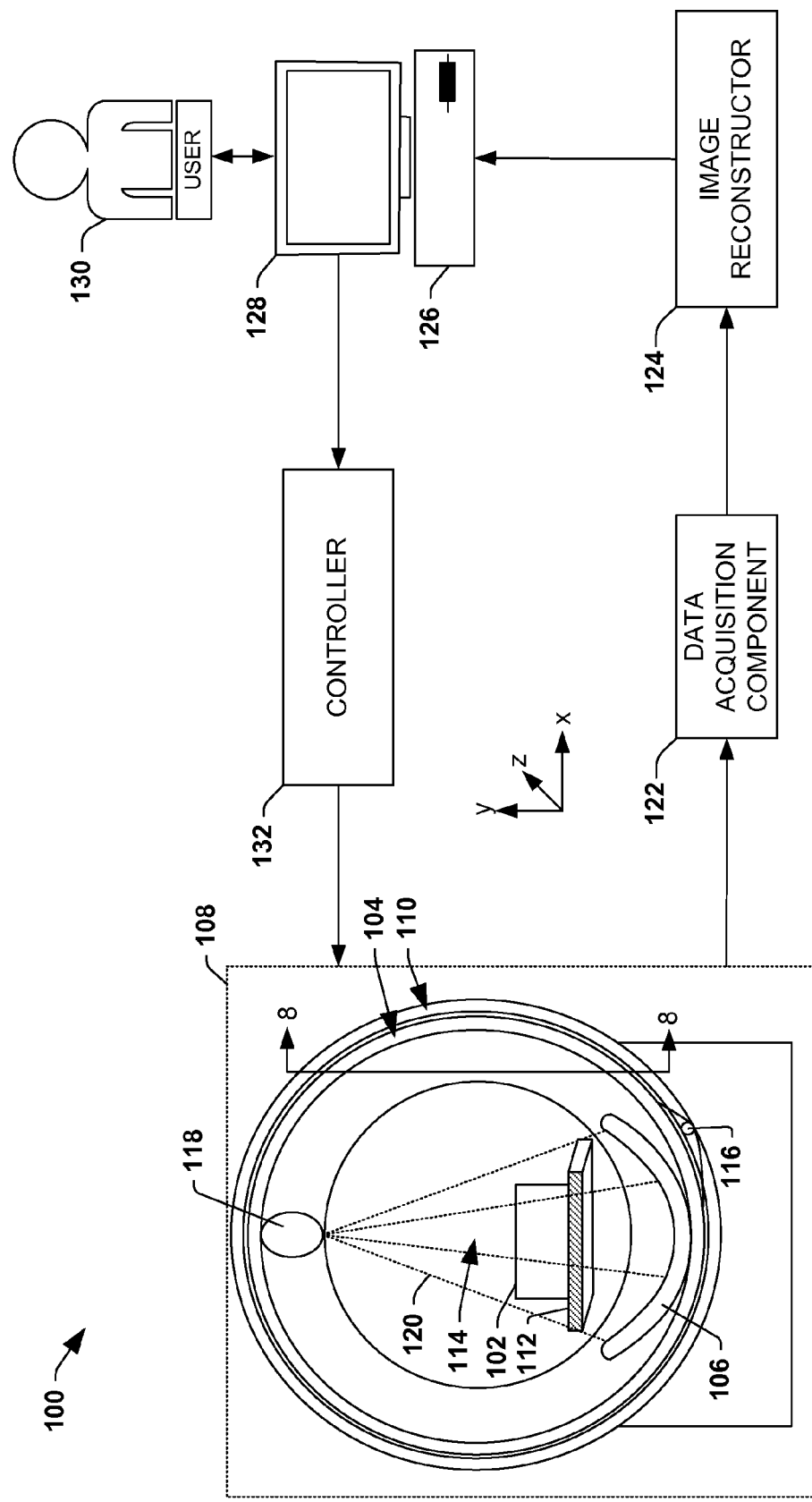
FIG. 1 is a schematic block diagram illustrating an example environment where a communication system such as described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a communication system for transferring information between two (or more) members. Typically, at least one of the members is movable (e.g., rotatable) relative to the other member and the two members are separated by an airgap. The communication system is comprised of at least a transmitter, a data-link (e.g., comprising at least a transmitting antenna or other transmitting medium and a receiving antenna or other receiving medium), and a receiver. The transmitter is configured to encode digital data using a character encoding scheme into a set of digital code words that are then mapped to a set of analog signals for transmission across the data-link. The transmitter may be configured to output more than two signal variations of an analog signal (e.g., where a transmitter configured to output merely two signal variations may be configured for 1-bit binary communications), and analog signals output by the transmitter may be transmitted in a variety of manners (e.g., optically, electromagnetically via radio frequency (RF) signals and/or current inducing electromagnetic fields, etc.) from the transmitter to the receiver via the data-link. The receiver may be configured to process an analog signal received from the transmitted and to estimate a digital output based upon the received analog signal. Typically, respective measurement intervals during which the analog signal is processed (e.g., which may represents one or more samples acquired during a given time to derive a decision/estimate) are indicative of more than one bit. For example, respective measurement intervals (e.g., decisions) may be indicative of at least 4 bits. In this way, the amount of information capable of being transferred across a data-link per second may be increased without altering hardware parameters of the data-link. For example, a data-link capable of transferring data at a rate of 1-2 gigabits/second using a convention 1-bit binary signaling technique may be capable of transferring data at a rate of 20 gigabits/second using techniques described herein (e.g., without altering hardware parameters of the data-link).

It may be appreciated that "noncontact," "contactless," and/or the like is used herein to refer to the ability to transfer information between or among bodies configured for relative movement, and should not be understood to necessarily preclude possible contact between or among such bodies for other purposes, including, for example, electrostatic discharge, exchange or transmission of data, mechanical drive or support, braking and safety mechanisms, low-voltage power transfer, high-voltage power transfer, etc. It may also be appreciated that in the present disclosure, except where otherwise clear from context, "gap" and "airgap" are used more or less interchangeably, and are not intended to be limited to air, it being possible for vacuum, oil, and/or other fluid and/or gas, and/or sliding and/or roller bearings or other such contrivances permitting relative movement to completely or partially fill such gaps or spaces.

FIG. 1 is an illustration of an example environment 100 where a communication system as provided for herein, including a transmitter, data-link (e.g., configured to transmit information across an airgap), and a receiver may be useful. More particularly, FIG. 1 illustrates an example computed tomography (CT) imaging modality that can be configured to acquire volumetric information regarding an object 102 under examination and generate images therefrom. It may be appreciated that the environment 100 is merely an example and is not intended to be interpreted in a limiting manner, such as necessarily specifying the location, inclusion, and/or relative arrangement of the components depicted therein. For example, a data acquisition component 122 as illustrated in FIG. 1 may be part of a rotating member 104 of an object examination apparatus 108, or more particularly may be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotating member 104 (at times referred to as a rotating gantry and/or a rotor) and a stationary member 110 (at times referred to as a stator). During an examination of the object(s) 102, the object(s) 102 can be placed on a support article 112, such as a bed or conveyor belt, that is selectively positioned in an examination region 114 (e.g., a hollow bore in the rotating member 104), and the rotating member 104 can be rotated about the object(s) 102 by a rotator 116 (e.g., motor, drive shaft, chain, etc.).

The rotating member 104 may surround a portion of the examination region 114 and may comprise one or more radiation sources 118 (e.g., an ionizing x-ray source, gamma-ray source, etc.) and a detector array 106 that is mounted on a substantially diametrically opposite side of the rotating member 104 relative to the radiation source(s) 118. During an examination of the object(s) 102, the radiation source(s) 118 emits fan, cone, wedge, and/or other shaped radiation 120 configurations into the examination region 114 of the object examination apparatus 108. It may be appreciated that such radiation may be emitted substantially continuously and/or may be emitted intermittently (e.g., a short pulse of radiation is emitted followed by a resting period during which the source(s) 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 (e.g., typically positioned on the rotating member 104) configured to convert the analog signals output by the detector array 106 into digital signals and/or to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example.

Information may be transmitted between components physically attached to the rotating member 104 (e.g., such as the detector array 106 and/or data acquisition component 122) and components that are not physically attached to the rotating member 104 (e.g., such as an image reconstructor 124) through a data-link. By way of example, the projection space data (at times referred to as image data even though it may be in projection space because it is used to reconstruct/generate images of the object) generated by the data acquisition component 122 may be transmitted via a communication system to an image reconstructor 124 positioned on the stationary side of the imaging modality. As may be described in more detail below, such a communication system may comprise, among other things, a transmitter (e.g., mounted to the rotating member 104), a data-link (e.g., comprising a transmitting antenna mounted to the rotating member 104 and a receiving antenna mounted to the stationary member 110), and a receiver (e.g., mounted to the stationary member 110). In this way, information may be transferred from the rotating member 104 to the stationary member 110. It may be appreciated that information may also be transmitted from the stationary member 110 to the rotating member 104 via such a communication system, with the location of the components reversed (e.g., such that the transmitter and transmitting antenna are mounted on the stationary member 110 and the receiver and receiving antenna are mounted on the rotating member 104). Further, such a communication system may be bi-directional, for example, with a first transceiver mounted on the rotating member 104 and a second transceiver mounted on the stationary member 110, for example. It may thus be appreciated that such a data-link (which may be contactless, for example) may be said to comprise a rotating portion (e.g., transmitting antenna, receiving antenna, transceiver, etc.) operably coupled to the rotating member 104 and/or a stationary portion (e.g., transmitting antenna, receiving antenna, transceiver, etc.) operatively coupled to the stationary member 110, for example.

The image reconstructor 124 is configured to receive the projection space data that is output by the data acquisition component 122 (e.g., or output from the communication system that communications information related to the data across an airgap separating the rotating member 104 from the stationary member 110). The image reconstructor 124 is also configured to generate image space data from the projection space data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive input from the terminal 126, such as user input for example, and to generate instructions for the object examination apparatus 108 indicative of operations to be performed. For example, the user 130 may desire to reexamine the object(s) 102 at a different energy level, and the controller 132 may issue a command instructing the support article 112 to reverse direction (e.g., bringing the object(s) 102 back into an examination region 114 of the object examination apparatus 102).

Figure 2:
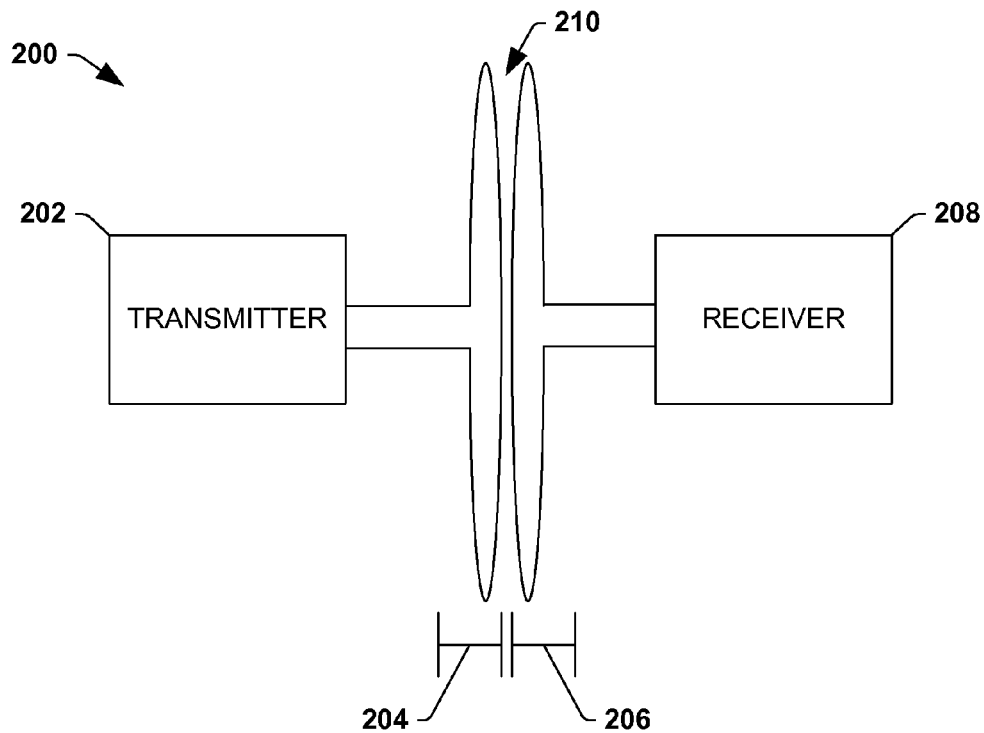
FIG. 2 illustrates a component block diagram of an example communication system.

FIG. 2 illustrates an example communication system 200 configured to communicate information between a rotating member (e.g., 104 in FIG. 1) and a stationary member (e.g., 110 in FIG. 1) via a contactless data-link. While the example communication system 200 provides for one-way communication, where information is transmitted from a transmitter 202 to a receiver 208, it may be appreciated that such a communication system 200 may be configured to provide for two-way communication. For example, the transmitter 202 and the receiver 208 may be replaced with transceivers respectively configured to perform the functions of both the transmitter 202 and the receiver 208. Further, in another embodiment, two-way communication may be achieved using two transmitters and two receivers (e.g., where a first transmitter/receiver combination is mounted to the rotating member and a second transmitter/receiver combination is mounted to the stationary member).

As illustrated, the example communication system 200 comprises a transmitter 202, a data-link comprised of a transmitting antenna 204 and a receiving antenna 206, and a receiver 208. By way of example, such a communication system 200 may be configured to communicate image data (e.g., indicative of detected radiation) and/or control information (e.g., gate-drive information and/or status information) from the rotating member (e.g., including components attached thereto) to the stationary member (e.g., including components attached thereto) and/or from the stationary member to the rotating member. As another example, such a communication system 200 may be configured to communicate control information (e.g., for controlling a radiation source, detector array, and/or other component(s) mounted to the rotating member) from the stationary member to the rotating member. Moreover, as described with respect to FIG. 1 and as will be further described with respect to FIG. 8, the transmitting antenna 204 and the receiving antenna 206 are typically separated by an airgap 210.

The example transmitter 202 is configured to receive digital data indicative of the information to be transmitted (e.g., which may include image data and/or control data) and is configured to generate (e.g., prepare and/or condition) an analog signal indicative of (e.g., representative of) the information. By way of example, the transmitter 202 may be configured to receive digital data via a first transmission medium (e.g., such an optical signal or other form of digital signal) and may be configured to convert the received digital data into an analog signal from which radio waves, for example, may be generated by the transmitting antenna 204. As will be described below, the transmitter 202 is configured to generate at least three different signals variations, where respective variations are representative of a different digital data set (e.g., or digital code word). That is, stated differently, the transmitter is configured to vary the signal between at least three different signal variations, where respective variations have a unique combination of amplitude, phase, frequency, and/or other signal characteristics. It may be appreciated that this is different than conventional CT transmitters configured for 1-bit binary signaling, where the transmitter is configured to output merely two signal variations (where a first signal variation is indicative of a first binary value "0" and a second signal variation is indicative of a second binary value "1"). In this way, respective decisions (e.g., yielded based upon one or more samples of the analog signal (e.g., as sampled by the receiver 208)) may be indicative of more than one bit, for example (e.g., may represent 2-bits of more of data).

As an example, suppose that a 256-bit message is to be transmitted from the transmitter 202 to the receiver 208. Using a conventional binary approach (e.g., where the transmitter 202 is configured to vary the signal between a first signal variation and a second signal variation), the receiver 208 may be required to make 256 decisions in order to reconstruct/estimate the 256-bit message. As such, information is communicated across the data-link bit-by-bit. As provided for herein, the transmitter 202 is configure to vary the signal between at least 3 variations, allowing multiple bits of data to be communicated concurrently (e.g., in the form of an analog signal). For example, when the transmitter 202 is configured to vary the signal between at least 16 variations (e.g., 2^4 variations), respective analog signals may be indicative of 4 bits of data. As such, the receiver 208 may make 64 decisions (e.g., 256/4) to reconstruct/estimate the 256-bit message. Thus, the number of samples may be reduced, thereby reducing the time it takes for the message to be communicated.

The analog signal(s) output by the transmitter 202 may be transmitted to a transmitting antenna 204 of the data-link. The transmitting antenna 204 is configured to convert the analog signal(s) into radio waves or into another type of communication signal through which information may be transmitted wirelessly.

Figure 8:
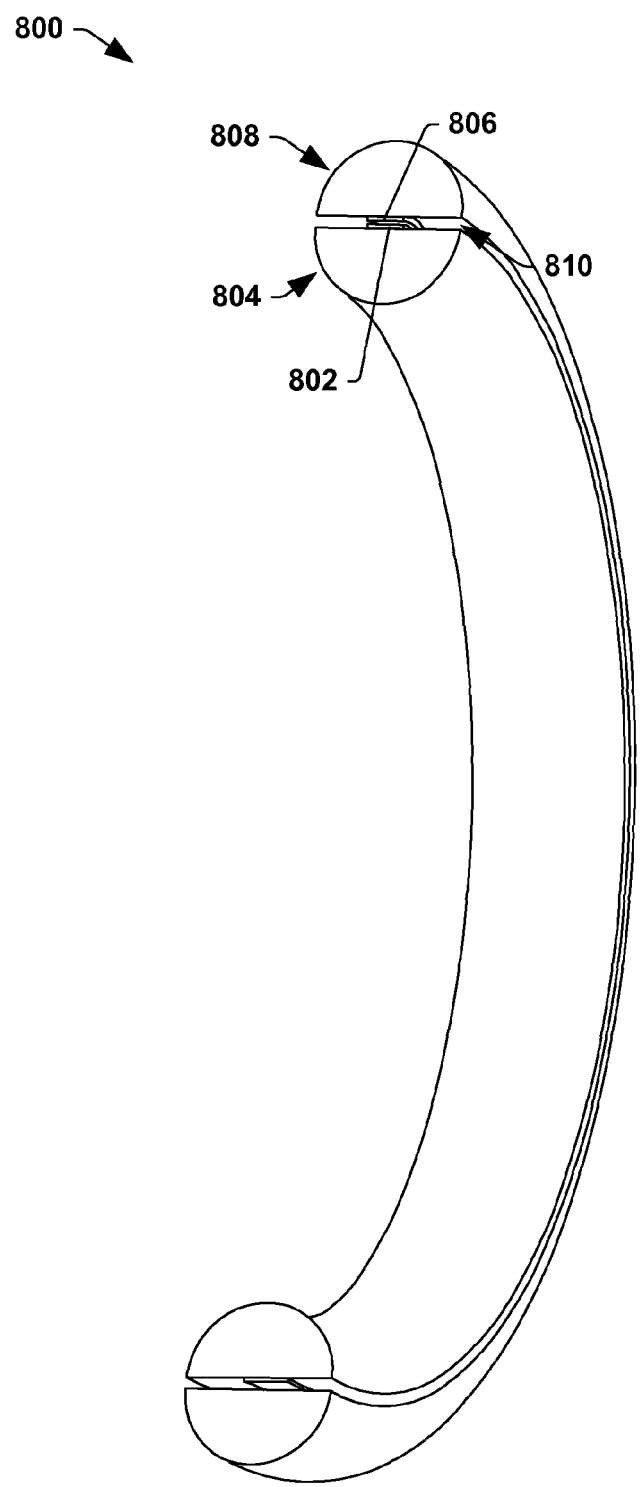
FIG. 8 illustrates an example rotating member and stationary member of a CT system separated by an airgap.

At least a portion of the radio waves output by the transmitting antenna 204 may be received by a receiving antenna 206 of the data-link (e.g., separated from the transmitting antenna 204 by an airgap 210, as will be further described with respect to FIG. 8). The receiving antenna 206 is configured to generate an analog signal in response to the detection of radio waves. Typically, the analog signal generated by the receiving antenna 206 substantially corresponds to the analog signal output by the transmitter 202, although some noise may be introduced into the analog signal during the transmission from the transmitting antenna 204 to the receiving antenna 206.

The example communication system 208 further comprises a receiver 208 configured to receive the analog signal generated by the receiving antenna 206 and to process the analog signal to estimate the digital data represented by the analog signal. That is, stated differently, the receiver 208 is configured to process the analog signal output by the receiving antenna 206 and to decode the signal based upon characteristics/properties of the analog signal to determine what digital code word the analog signal is intended to represent.

Figure 3:
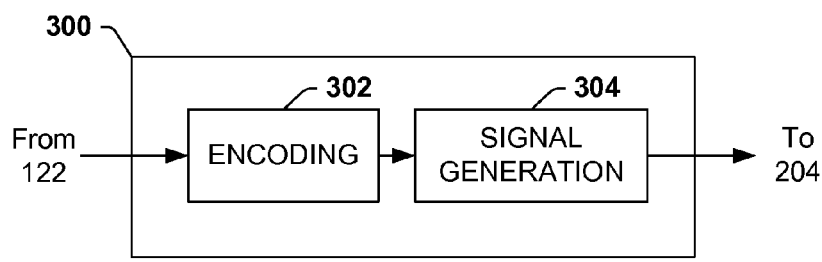
FIG. 3 illustrates a component block diagram of an example transmitter.

FIG. 3 illustrates a component block diagram of an example transmitter 300 (e.g., 202 in FIG. 2) configured to receive the digital data (e.g., such as from a data acquisition component 122 in FIG. 1) and to output an analog signal indicative of the received digital data for transmission across an airgap (e.g., via a data-link). It may be appreciated that the components described with respect to FIG. 3 are merely example components and that the transmitter 300 may comprise additional and/or different components to perform other functions not described herein. Moreover, the functions described herein as being performed by a single component may be performed by a combination of components, and/or functions described as being performed by two or more components may be performed by a single component.

The example transmitter 300 comprises an encoding component 302 and a signal generation component 304. The encoding component 302 is configured to receive the digital data, which may be encoded according to a first encoding scheme, and to encode the digital data according to a second encoding scheme to form a set of one or more digital code words representative of the digital data. That is, stated differently, the encoding component 302 is configured to convert digital data from a first encoding scheme to a second encoding scheme that may be desirable for signal generation and/or for transmission via the data-link. By way of example, the encoding component 302 may convert the incoming data from a 256-bit message to 4-bit sequences (e.g., 4-bit code words) (e.g., such that the 256 bit message is divided into 64, O-bit code words) in order to facilitate transmission of data through the data-link. It may be appreciated that where the digital data, as encoded when received by the transmitter 300, is capable of being mapped to an analog signal, no such conversion may occur and thus the encoding component 302 may be optional, for example.

The desired encoding scheme may be a function of, among other things, the signal-to-noise ratio of the data-link and/or other characteristics of the data-link (e.g., such as bandwidth). By way of example and not limitation, desired encoding schemes may include, but are not intended to be limited to, binary encoding schemes, truncated binary encoding schemes, and/or non-binary encoding schemes. It may be appreciated that traditionally, an encoding component of a communication system for a CT modality has been configured to encode data into a 1-bit binary encoding scheme, where respective signals transmitted across the data-link are indicative of a single bit of information (e.g., or single-bit code words). Thus, a 256-bit message may be encoded into 256 1-bit code words, for example. As provided for herein, where a binary encoding scheme is utilized to encode the data, data may be encoded into 2-bit or greater sequences. For example, the 256-bit message may be encoded into 2-bit code words, 3-bit code words, etc. It may be appreciated that where the desired coding scheme is a non-binary coding scheme, respective messages may be non-binary (e.g., such that the possible number of different signal variations generated by the signal generation component 304 is more than two, but not necessarily an exponential of two (e.g., 4, 8, 16, 32, 64, etc.)). For example, in one embodiment, the encoding component 302 may encode the data such that a message may be indicative of three possible values (e.g., 0, 1, 2, or other discrete sets of signals), thus requiring the signal generation component 304 to be configured to generate at least three distinctive signal variations (e.g., a first signal variation representative a "0," a second signal variation representative of a "1," and a third signal variation representative of a "2").

The signal generation component 304 of the transmitter 300 is configured to map respective digital code words representing the received digital data into one or more analog signals for transmission across the data-link. That is, stated differently, the signal generation component 304 is configured to generate/condition an analog signal for respective digital code words to be transmitted across the data-link, where at least one property/characteristic of the signal is a function of the digital code word being sent.

By way of example, a database may comprise a mapping that correlates respective possible digital code words to a signal configuration (e.g., such that there is at least a one-to-one ratio of digital code words to signal configurations). For example, where the encoding component 302 is configured to encode data into 4-bit sequences (e.g., meaning there are 16-possible combinations for the four bits), the database may comprise a map that correlates respective bit sequences/combinations to one of 16 different signal configurations. Thus, the signal generation component 304 may be configured to generate at least 16 different signal configurations (e.g., such that each of the 16-possible 4-bit sequences is mapped to a different signal configuration). During an increment of time when a first digital code word is to be transmitted across the data-link, the signal generation component 304 may map a first digital code word into a first analog signal by selecting, from at least three possible signal configurations comprised in the database, a first signal configuration corresponding to the first digital code word and by generating a first analog signal according to the selected first signal configuration. Likewise, during an increment of time when a second digital code word is to be transmitted across the data-link, the signal generation component 304 may map the second digital code word to a second analog signal by selecting, from the at least three possible signal configurations, a second signal configuration corresponding to the second digital code word and by generating a second analog signal according to the selected second signal configuration. It may be appreciated that unless that first digital code word and the second digital code word are the same (e.g., the same sequence of 4-bits in the scenario where data is encoded into 4-bit sequences), the first and second signal configurations are different (e.g., causing at least one characteristic to differ between the first analog signal and the second analog signal).

Typically, the first analog signal is generated and/or transmitted across the data-link at a different time interval than the second analog signal (e.g., so that the first analog signal is sampled by a receiver prior to the second analog signal), and thus the first and second analog signals may be said to be temporally distinct. That is, the first and second analog signals may be generated and/or transferred sequentially (e.g., as opposed to concurrently). It may be appreciated that the increment of time for sending respective code words (or rather their corresponding analog signals) across the data-link may be in the nanoseconds, microseconds, etc. and may be a function of, among other things, the bandwidth of the data-link. Moreover, it may be appreciated that instead of generating separate signals for respective digital code words (e.g., such that there is some identified break between a first signal representative of a first digital code word and a second signal representative of a second digital code word), the signal generation component 304 may be configured to substantially continuously output a signal, but may be configured to vary one or more characteristics of the signal to communication respective digital code words across the data-link. Thus, the first and second signals may be visually represented as a single, continuous signal having at least one characteristic that changes between mapping the first digital code word and mapping the second digital code word to the analog signal.

Figure 4:
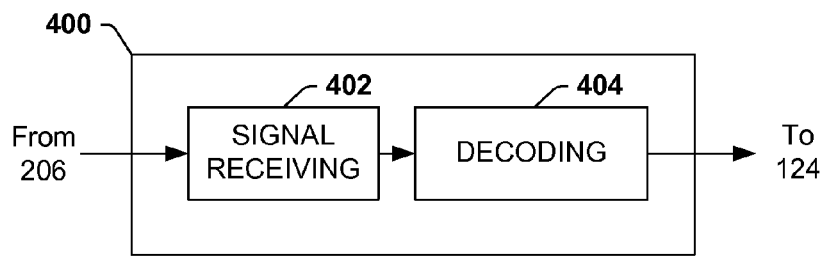
FIG. 4 illustrates a component block diagram of an example receiver.

FIG. 4 illustrates a component block diagram of an example receiver 400 (e.g., 208 in FIG. 2) configured to receive an analog signal from a receiving antenna (e.g., 206 in FIG. 2) of a data-link and to output digital data (e.g., such as to an image reconstructor 124 in FIG. 1) yielded from the analog signal. It may be appreciated that the components described with respect to FIG. 4 are merely example components, and the receiver 400 may comprise additional and/or different components to perform other functions not described herein. Moreover, the functions described herein as being performed by a single component may be performed by a combination of components, and/or functions described as being performed by two or more components may be performed by a single component.

The example receiver 400 comprises a signal receiving component 402 and a decoding component 404. The signal receiving component 402 is configured to receive the analog signal from the data-link and to condition the analog signal for the decoding component 404. By way of example, the signal receiving component 402 may filter aspects of the analog signal such as frequencies outside of a specified range and/or otherwise process the analog signal to improve or enhance the quality of one or more characteristics of the signal (e.g., such as qualities and/or characteristics that the decoding component 404 may utilize to decode the signal). For example, in one embodiment, the signal receiving component 402 may amplify the analog signal to increase the power of the received signal prior to a decoding process. It may be appreciated that although such a signal receiving component 402 may improve the accuracy of the decoding and/or otherwise enhance the decoding process, in another embodiment, the receiver 400 may not comprise a signal receiving component 402 as described herein. As such, the received signal may be transmitted from the receiving antenna (directly) to the decoding component 404, for example.

The decoding component 404 is configured to decode the received signals. That is, stated differently, the decoding component 404 is configured to map the received analog signal back to the digital code words (e.g., according to the same or substantially similar mapping scheme as utilized by the signal generation component 304 in FIG. 3) by identifying characteristics of the analog signal and determining which digital code word (e.g., listed in the mapping scheme) corresponds to a signal configuration matching the identified characteristics. In this way, the analog data is converted back into digital data that may be utilized by other components of the CT system, for example.

The decoding component 404 may be configured to decode the analog signal by sampling the analog signal and identifying a signal configuration, from at least three possible signal configurations, that matches the sampled analog signal configuration. That is, stated differently, the decoding component may be configured to compare one or more measured characteristics of the signal during a measurement interval to respective characteristics of at least three possible signal configurations, to determine a matching signal configuration that describes characteristics of an analog signal that match the measured characteristics. Respective signal configurations of the at least three possible signal configurations may be mapped to an associated digital code word (e.g., according to a same mapping scheme as utilized by the signal generation component 304 of FIG. 3 to determine how characteristics of a signal are to be generated/conditioned based upon a received digital code word). Thus, by determining a matching signal configuration, a digital code word corresponding to the matching signal configuration may be identified. In this way, an analog signal may be mapped to digital data (e.g., a digital code word), which corresponds to and/or is the same as the digital code word input into the signal generation component 304 to generate the analog signal now being sampled by the decoding component 404. Thus, the transmitter maps a digital code word to an analog signal and the receiver 400 maps the analog signal back to the digital code word via the sampling and comparing technique described herein.

It may be appreciated that although the number of possible signal variations is discrete (e.g., for example 16 possible signals configurations may be utilized when 4-bits of data are to be mapped to a signal), in practice the sampled signal may not correspond to any of the 16 possible signal configurations (e.g., described in a database) due to noise introduced into the signal during the transmission of the signal via the data-link, for example. As such, the decoding component 404 may be configured to estimate which of the possible signal configurations best approximates the sampled signal. Thus, some errors may occur during the decoding process by the decoding component 404 due to noise introduced in the signal output by the signal generation component 304 via the data-link, for example. Moreover, a matching signal configuration may not literally match characteristics of the sampled analog signal. Rather, a matching signal configuration may be defined is a signal configuration that approximates the sampled analog signal. That is, the sampled analog signal may comprise one or more properties/characteristics that fall within a tolerance of a particular signal configuration such that the sampled analog signal can be said (e.g., determined) to correspond or match that particular signal configuration as opposed to other possible signal configurations described in a mapping scheme, for example.

FIG. 5 illustrates an example mapping scheme 500 that may be utilized by a signal generation component (e.g., 304 in FIG. 3) to generate an analog signal based upon a digital code word 502 to be conveyed across a data-link and/or by a decoding component (e.g., 404 in FIG. 4) to estimate a digital code word 502 based upon a processed analog signal, for example. It may be appreciated that the example mapping scheme 500 describes a 4-bit encoding scheme, where respective digital code words 502 are a 4-bit sequence of binary values. However, other encoding schemes are also contemplated, and thus an implementation of the mapping scheme 500 may comprise other/different digital code words than illustrated. Moreover, the message may be encoded into a mapping scheme that comprises more bits than the digital data itself. By of example, as will be described in more detail below, a digital message comprised of 14 bits may be mapped into four, 4-bit digital code words and transmitted across the data-link. As such, 16 bits may be transmitted across the data-link to convey a 14-bit message, for example, where additional bits may mitigate communication errors, for example.

As illustrated, respective digital code words 502 are mapped to a respective signal configuration 504 specifying one or more signal characteristics of a signal that is to be generated when the digital code word 502 is to be represented by the analog signal. For example, when the digital code word "0010" is to be mapped to an analog signal, the signal generation component may look to the mapping scheme 500 and determine that the generated signal is to comprise a phase of 0 degrees and a frequency of 300.2 MHz and may generate an analog signal comprising such characteristics. Similarly, when the decoding component samples a signal and determines that the analog signal comprises a phase of approximate 270 degrees and a frequency of approximately 300.1 MHz, the decoding component may determine that the analog signal is intended to represent the digital code word "1101," for example.

It may appreciated that although the example mapping scheme 500 describes using phase and frequency characteristics of a signal to discriminate between digital code words, other characteristics may also and/or instead be utilized. For example, a mapping scheme may use amplitude, phase, frequency and/or other signal characteristics to differentiate between digital code words. Further, while the example mapping scheme 500 describes using two signal characteristics to create 16 difference signal variations (e.g., such that respective digital code words are associated with a unique signal variation), merely one signal characteristic may be utilized and/or a combination of more than two signal characteristics may be utilized. For example, in another embodiment, the signal configuration may map respective digital code words to a unique amplitude value (e.g., such that no two digital code words are mapped to the same amplitude value). As such, merely the amplitude of the analog signal may be utilized to determine which digital code word the analog signal is intended to represent.

FIG. 6(a)-6(b) are intend to illustrate how an 8-bit message may be communicated across a data-link using a conventional 1-bit binary signaling technique and using the communication system provided herein (e.g., where respective signals are representative of more than 1-bit of data).

More particularly, FIG. 6(a) illustrates a plot 600 describing the transfer of data using a 1-bit binary signal technique. The x-axis illustrates time and the y-axis illustrates a voltage of the signal. As previously described, using a 1-bit binary signaling technique, data is communicated across the data-link bit-by-bit. Binary zeros may be conveyed by generating an analog signal comprising a first voltage and binary ones may be conveyed by generating an analog signal comprising a second voltage. A receiver of the communication system is configured to periodically sample a signal 602 and a decision may be made to determine whether the sampled portion of the signal is representative of a "0" or a "1" based upon one or more samples acquired during a specified measurement interval. By compiling information acquired during a plurality of measurement intervals, the 8-bit message may be derived. In the illustrated plot 600, boundaries of respective measurement intervals are illustrated by dashed lines and the arrows between the dashed lines illustrate the measurement intervals (e.g., where a decision regarding whether a portion the signal 602 during a measurement interval is representative of a "0" or a "1" may be made at the end of the measurement interval for that portion based upon one or more samples taken during the measurement interval). It may be appreciated that in FIG. 6(a), respective measurement intervals may represent 1 nanosecond, for example. As such, a new measurement interval begins every 1 nanosecond, and it may take approximately 8 nanoseconds for the entire 8-bit message to be communicated across the data-link.

FIG. 6(b) illustrates a plot 604 describing the transfer of data using a signaling technique described herein where more than 1-bit may be communicated per signal. By way of example, the illustrated plot 604 is intended to describe how 4-bits of information may be communicated per signal. The x-axis illustrates time and the y-axis illustrates a voltage of the signal. It may be appreciated that for purposes of simplicity, respective code words are identified merely based upon voltage in this example. However, as described with respect to FIG. 5, additional and/or different characteristics of a signal may be utilized in some embodiments to identify code words (e.g., where using multiple characteristics may promote accuracy). A receiver (e.g., 400 in FIG. 4) of the communication system is configured to periodically sample a signal 606 and a decision may be made to determine which 4-bit digital code word is represented during respective sample times based upon samples acquired during a specified measurement interval. By compiling information acquired during a plurality of measurement intervals, the 8-bit message may be derived. In the illustrated plot 604, boundaries of respective measurement intervals are illustrated by dashed lines and the arrows between the dashed lines illustrate the measurement intervals (e.g., where a decision regarding which 4-bit digital code word is represented in the signal during a particular measurement interval may be made at the end of the particular measurement intervals based upon one or more samples taken during the measurement interval). It may be appreciated that in FIG. 6(b), respective measurement intervals may represent 1.5 nanoseconds, for example. As such, a new measurement interval begins every 1.5 nanoseconds, and it may take approximately 3 milliseconds for the entire 8-bit message to be communicated across the data-link.

By comparing FIG. 6(a) to FIG. 6(b), it can be seen that the 8-bit message is conveyed more quickly (e.g., in 3 nanoseconds) using the communication system described herein than it is conveyed using the convention 1-bit binary signaling technique (e.g., which took 8 nanoseconds to convey the entire message). Moreover, although the sampling intervals increased in time when using the communication system described herein (e.g., because a more accurate estimate may be required to estimate which of 16 possible digital words is being conveyed, as compared to which of 2 possible digital words is being conveyed in the convention 1-bit technique), the total time to convey the message may be decreased. It may be appreciated that in practical CT applications, the throughput of a data-link may be increased from 1-2 Gbits/second to a significantly higher rate (e.g., approaching a theoretical limit, such as may be defined in channel capacity theory using a realistic bandwidth and signal-to-noise ratio, for example) of 20 Gbits/second using such an approach where the signal-to-noise ratio is high (e.g., where the data-link causes little to no noise to be introduced into the analog signal).

Figure 7:
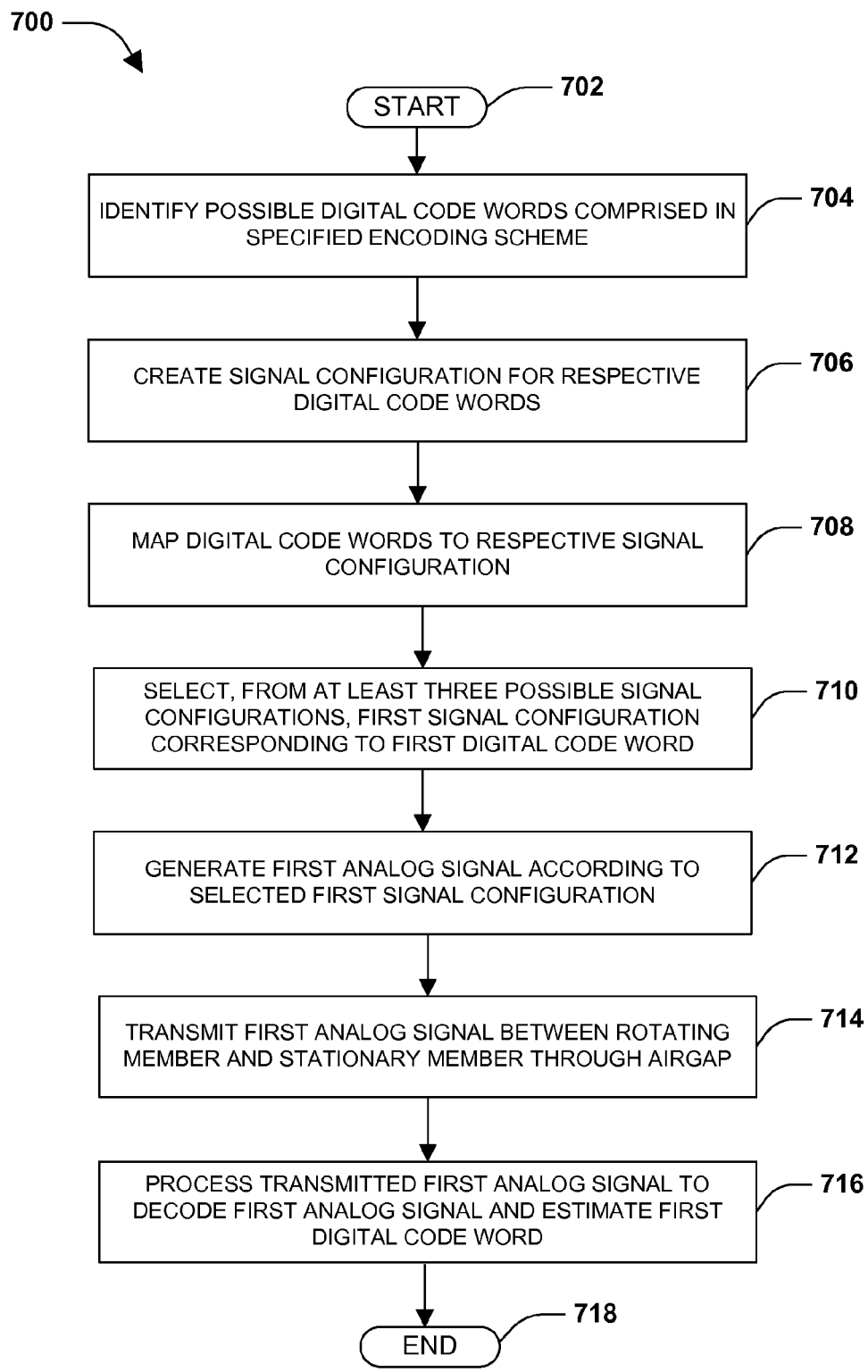
FIG. 7 illustrates an example flow diagram providing an example method for communicating information across a contactless data-link of a CT system.

FIG. 7 illustrates an example method 700 for communicating information between a rotating member and a stationary member of a computed tomography (CT) system (e.g., from to rotating member to the stationary member and/or from the stationary member to the rotating member). It may be appreciated that the illustrated arrangement of the acts is merely provided as an example. That is, to the extent practical, other arrangements (e.g., orderings) of the acts described herein are also contemplated. Moreover, at least some of the example acts may be optional. Thus, the scope of the disclosure, including the scope of the claims, it not intended to be limited by the example method 100.

The example method 700 begins at 702, and possible digital code words comprised in a specified encoding scheme are identified at 704. That is, stated differently, to generate an analog signal representative of information comprised in digital data (e.g., received by a transmitter), the data may be required to be arranged according to a specified encoding scheme. Such an encoding scheme may be a binary encoding scheme, a truncated binary encoding scheme, and/or a non-binary encoding scheme, for example. The arrangement of the digital data according to the specified encoding scheme may form what can be referred to as digital code words (e.g., or bit patterns/sequences). For example, a 4-bit encoding scheme may specify that the digital data is to be transmitted between the rotating member and the station member in 4-bit increments or rather that respective analog signals are to represent 4-bits of the digital data. As such, the encoding scheme may provide for 16 possible bit sequences (e.g., $2^4$ bit sequences) or 16 possible code words (e.g., 0000, 0001, 0010, 0011, etc.). Thus, the possible code words may be identified and/or derived according to the specified encoding scheme.

It may be appreciated that numerous encoding schemes (e.g., ASCII, EBCDIC, UTF-8, etc.) for communicating information (e.g., and/or for representing digital data comprising such information) are contemplated for use as the specified encoding scheme. Further, it may be appreciated that the encoding scheme that is specified may be dependent upon, among other things, the specific CT application and/or the signal-to-noise ratio of the data-link. By way of example, where the signal-to-noise ratio is high, little noise may be introduced into an analog signal as it is transmitted across the data-link. As such, a receiver may be able to accurately discriminate (e.g., with little to no error) a greater number of different signals than when the signal-to-noise ratio is lower. Thus, an 8-bit encoding scheme (e.g., requiring 256 (2^8) different signal configurations) may be utilized when the signal-to-noise ratio is high and a 4-bit encoding scheme (e.g., requiring 16 (2^4) different signal configurations) may be utilized when the signal-to-noise ratio is lower (e.g., because a greater amount of noise may be present relative to the signal making it more difficult to discern the signal from the noise). That is, because of additional noise, an encoding scheme that does not provide for transferring as much information per signal may be implemented to allow the receiver to accurately estimate what information (or what digital code word) is represented by respective signals.

In the example method 700, a signal configuration for respective digital code words is created at 706, and the signal configurations are mapped to the digital code words at 708. That is, stated differently, a signal configuration is created for each of the digital code words identified at 704. The signal configurations respectively specify a value for one or more characteristics/properties of a signal (e.g., amplitude, frequency, phase, etc.) to be generated when the corresponding digital code word is to be mapped to an analog signal. For example, where 64 possible digital code words are identified (e.g., in an 8-bit encoding scheme), 64 signal configurations may be created at 706. It may be appreciated the respective signal configurations created at 706 are unique. That is, the value or combination of values specified in a first signal configuration is different that the value or combination of values specified in remaining signal configurations. For example, a first signal configuration, mapped to a first digital code word, may provide for creating a signal that has a frequency of 300 MHz and a phase of 90 degrees, and the other signal configurations created at 706 may not comprise this combination of 300 MHz and 90 degree phase (e.g., or it may be difficult/impossible to distinguish a signal representative of a first digital code word (e.g., generated according to a signal configuration mapped to the first digital code word) from a signal representative of a second digital code word (e.g., generated according to a signal configuration mapped to the second digital code word).

It may be appreciated that mapping the signal configurations to a respective code word at 708 may comprise pairing, in a table or other data structure, a first signal configuration to a first digital code word, a second signal configuration to a second digital code word, etc. In this way, when a digital code word is to be mapped to an analog signal by a transmitter, for example, the transmitter can search the data structure to identify a signal configuration corresponding to the digital code word and can generate an analog signal that comprises characteristics matching the identified signal configuration.

It may also be appreciated that as previously described, information representing more than 1-bit of digital data is to be transmitted in a signal. For example, respective signals may represent at least 2-bits of data. Given that the information is representative of more than 1-bit of digital data (e.g., representative of more than a "0" or a "1"), the specified encoding scheme typically comprises at least three possible digital code words, and thus at least three possible signal configurations are created at 706 in the example method 700. Moreover, the encoding scheme may be non-binary and thus one or more code words may represent a non-binary value.

At 710 in the example method 700, a first signal configuration corresponding to a first digital code word is selected, from the at least three possible signal configurations (e.g., created at 706), and a first analog signal is generated at 712 according to the selected first signal configuration. That is, stated differently, when a first portion of the digital data, corresponding to a first digital code word, is to be transmitted from a transmitter to a receiver via a data-link, the first portion of digital data, that is the first digital code word, is mapped to an analog signal by identifying, from the database, a signal configuration corresponding to the first digital code word and generating/conditioning an analog signal comprising characteristics/properties that match the identified signal configuration. Similarly, when a second portion of the digital data, that is a second digital code word, is to be transmitted from the transmitter to the receiver, the second digital code word may be mapped to a second analog signal according to a signal configuration corresponding to the second digital code word.

By way of example and not limitation, suppose that a 256-bit digital message is to be communicated to the receiver of a communication system. The 256-bit digital message may be divided into 4-bit segments, or digital code words, to enable transmission of the information comprised in the digital message across a data-link. When a first 4-bit segment, or first digital code word, is to be transmitted across the data-link, the first digital code word may be identified in a look-up table, for example, and a signal configuration corresponding to the first digital code word may be selected. Using the selected signal configuration, a first signal may be generated that comprises characteristics specified in the selected signal configuration. Subsequently, when a second 4-bit segment, or second digital code word, is to be transmitted across the data-link, the second digital code word may be identified in the look-up table and a signal configuration corresponding to the second code word may be selected. Using the selected signal configuration corresponding to the second digital code word, a second signal may be generated that comprises characteristics specified in the selected signal configuration. It may be appreciated that if the second 4-bit segment matches the first 4-bit segment (e.g., such that the bit sequence is identical), the first and second signals may be substantially similar (e.g., identical) and thus the transmitter may generate the first analog signal for a prolonged period of time (e.g., such that two samples are yielded from the first analog signal). However, where the first and second 4-bit segments do not match, the first analog signal may comprise one or more characteristics that are different than the second analog signal.

It may be appreciated that while continued reference is made herein to first and second signals, a visual representation of the first and second signals may illustrate a single, continuous signal, where a first portion of the signal represents the first digital code word and a second portion of the signal represents the second digital code word. Thus, as used herein, the first signal and the second signal may not be visually disjoined, and/or the first and second signals may be part of a continuous waveform, where a first portion of the waveform represents the first signal and a second portion of the waveform represents a second signal (e.g., optionally comprising a transition portion between the first and second signals). In one embodiment, the first and second analog signals are temporally distinct. That is, the first signal is generated at a different time than the second signal (e.g., although the signals may be generated back-to-back).

At 714 in the example method 700, the first analog signal is transmitted between the rotating member and the stationary member through an airgap separating the rotating member and the stationary member. By way of example, a transmitter configured to generate the first analog signal may be physically coupled to the rotating member and the receiver configured to receive the first analog signal and sample the signal may be physically coupled to the stationary member of a CT system. In order to provide for rotating the rotating member relative to the stationary member, the rotating member may be separated from the stationary member via an airgap and the analog signal may be electromagnetically and/or otherwise transferred from a transmitting antenna to a receiving antenna (e.g., which may be separated by less than an inch). The second analog signal and subsequent analog signals may likewise be transmitted between the rotating member and the stationary member though an airgap via a data-link, for example.

At 716 in the example method 700, the transmitted first analog signal is processed to decode the first analog signal and to estimate the first digital code word from the first analog signal. That is, stated differently, the transmitted first analog signal is sampled during a measurement interval and decoded to determine what digital code word is intended to be represented by the first analog signal. It may be appreciated that during the generation and/or transmission of the first analog signal, noise may have been introduced into the first analog signal. As such, the sampled signal may not be identical to the signal intended to be generated and/or generated at 712 in the example method 700. Thus, a receiver configured to decode the first analog signal may be configured to estimate which of several potential digital code words the first analog signal is intended to represent.

By way of example, when a sample of the first analog signal is acquired, properties/characteristics of the first analog signal may be determined and compared to a data structure (e.g., a look-up table of signal configurations, such as the look-up table utilized when generating the analog signal) to identify a signal configuration that specifies signal characteristics matching the characteristics of the sampled analog signal. From this identification, it may be determined which digital code word the sampled analog signal is intended to represent. However, given that noise may be introduced into the signal during the transmission of the signal across the data-link, the characteristics of the signal may not match the specified characteristics of any signal configuration. As such, a receiver, for example, may be configured to determine which the signal configurations specifies signal characteristics that substantially match (e.g., within a reasonable/specified tolerance) the characteristics of the sampled signal.

The example method 700 ends at 718.

As previously described, it may be appreciated that noise may be introduced into the signal during transfer of the signal across the data-link. As such, the signal that is received by the receiver and decoded may be different than the signal generated by the transmitter. Thus, one or more characteristics of the received analog signal may not precisely match characteristics listed in a table of signal configurations (e.g., signal configuration 504 illustrated in FIG. 5). By way of example, an analog signal having a frequency of 299 MHz may be received, but 299 MHz may not be a frequency listed in a table of signal configurations. As such, the receiver may be configured to estimate which of the digital code words the analog signal is intended to represent by identifying which of the signal configurations in the table, for example, most closely approximates the characteristics of the received signal. Given that digital code word is estimated (e.g., because there is not an exact match between the signal configurations in the table and the signal characteristics of the received signal), it is possible that an incorrect digital code word may be identified or selected.

In one embodiment, to increase the likelihood that the correct code word is identified, the receiver, for example, may be configured to compile at least an estimate of a first digital code word and an estimate of a second digital code word to generate a communicated message and to estimate an actual message intended to be transmitted between the rotating member and the stationary member based upon the communicated message. For example, a first 4-bit digital code word can be combined with a second 4-bit digital code word to generate an 8-bit communicated message, and an actual message (that was intended to be transmitted between the rotating member and the stationary member) may be estimated based upon the 8-bit communicated message. Stated differently, the receiver may be configured to examine a larger portion of data (e.g., 8-bits) to determine whether that data (e.g., a compilation of two 4-bit digital code words) does not fail some test which would indicate that at least one of the digital code words that have been selected is not correct.

By way of example, and not limitation, in one embodiment, the system may be configured to communicate a 6-bit message across the data-link and may encode the message into two 4-bit increments for mapping to first and second analog signals (e.g., a first analog signal communicating the first 4-bits and a second analog signal communicating the second 4-bits). It may be appreciated that such an encoding may introduce two bits of data that were not initially included in the 6-bit message (e.g., thus the number of bits to which the data is encoded may be more than the number of bits that comprise the message). It may also be appreciated that whereas there are merely 64 possible sequence configurations (of 0's and 1's) for a 6-bit message (e.g., $2^6$ possible configurations), there are 256 possible sequence configurations (of 0's and 1's) for an 8-bit message (e.g., $2^8$ possible configurations). In such a situation, therefore, merely 64 of the 256 possible configurations of sequences for the 8-bit message may be utilized to derive a 6-bit message from the 8 bits of data that are transmitted across the data-link. As such, as described at 716 in the example method 700 of FIG. 7, a decision may be made (e.g., such as by consulting a table as illustrated in FIG. 5) as to which 4-bit code word each of the two analog signals represents (e.g., because each of the analog signals is intended to represent 4 bits of data). Subsequently, the two estimated digital code words may be combined (e.g., to form an 8-bit communicated message) and it may be determined if the 8-bit communicated message corresponds to one of the 64 configurations out of the 256 possible configurations. Stated differently, the sequence of the 8 bits in the communicated message is compared to a list of 64 preselected 8-bit sequences for communicating a 6-bit message. If the 8-bit sequence corresponds to one of the utilized 64 configurations, the 8-bit sequence may be decoded to a 6-bit message. For example, a table may comprise 64 of the 256 possible configurations of 8-bit sequences where each of the 64 configurations in the table may be associated with a corresponding 6-bit sequence. Thus, if the 8-bit communicated message matches one of the predefined 64 configurations in the table, the corresponding 6-bit message may be selected (e.g., thus estimating the 6-bit message from the communicated 8-bit message). If the 8-bit communicated message does not correspond to one of the 64 configurations (e.g., and instead corresponds to one of the remaining 192 configurations that do not have an associated G-bit message), then it may be determined that at least one of the decisions made with respect the analog signals is incorrect (e.g., the first 4-bit code word estimated from the first analog signal is incorrect and/or the second 4-bit code word estimated from the second analog signal is incorrect). That is, if the communicated 8-bit message does not correspond to one of the utilized 64 configurations, it may be determined that at least one of the digital code words that forms the 8-bit communicated message was estimated incorrectly. As such, the receiver may estimate from the 8-bit communicated message which of the 64 configurations that do have an associated 6-bit message is most likely to be the 8-bit sequence that was intended to be transmitted through the data link. Thus, an estimate is made based upon a combination of estimated digital code words (e.g., to provide a check of the estimates made at 716).

FIG. 8 illustrates a cross-sectional view 800 (e.g., taken along line 8-8 in FIG. 1) of a data-link comprising a transmitting antenna 802 (e.g., 204 in FIG. 2) physically coupled to a rotating member 804 (e.g., 104 in FIG. 1) and a receiving antenna 806 (e.g., 206 in FIG. 2) physically coupled to a stationary member 808 (e.g., 110 in FIG. 1). It may be appreciated that in another embodiment, the placement of the transmitting and receiving antennas may be reversed. That is, the transmitting antenna 802 may be physically coupled to the stationary member 808 and the receiving antenna 806 may be physically coupled to the rotating member 804.

The rotating member 804 is typically separated from the stationary member 808 by an airgap 810 that is defined by a space between the rotating member 804 and the stationary member 808 and is configured to enable rotation of the rotating member 804 relative to the stationary member 808. Typically the transmitting antenna 802 is mounted on the rotating member 804 within and/or adjacent the airgap 810 and a receiving antenna 806 is mounted on the stationary member 808 within and/or adjacent the airgap 810, although other arrangements are contemplated. Thus, the transmitting antenna 802 may be configured to emit radio waves or other electromagnetic fields through the airgap 810 in the direction of the receiving antenna 806, which is positioned on a diametrically opposite side of the airgap 810 relative to the transmitting antenna 802. The distance between the transmitting antenna 802 and the receiving antenna 806 may be small given that the airgap 810 is typically less than 20 mm, although it may be more than 20 mm (e.g., such as up to a few inches).

It may be appreciated that although the foregoing cross-sectional view 800 describes a radial airgap 810 (e.g., between the entirety of the outer circumference of the rotating member 804 and entirety of the inner circumference of the stationary member 808), it may be appreciated that the airgap 810, transmitting antenna 802, and/or receiving antenna 806 may be arranged differently than the example arrangement. For example, in another embodiment, the airgap 810 may be planar (e.g., where the rotating member 804 and the stationary member 808 face one another, as opposed to being concentric), for example, and the transmitting antenna 802 may be mounted on a planar surface of the rotating member 804, for example.

Figure 9:
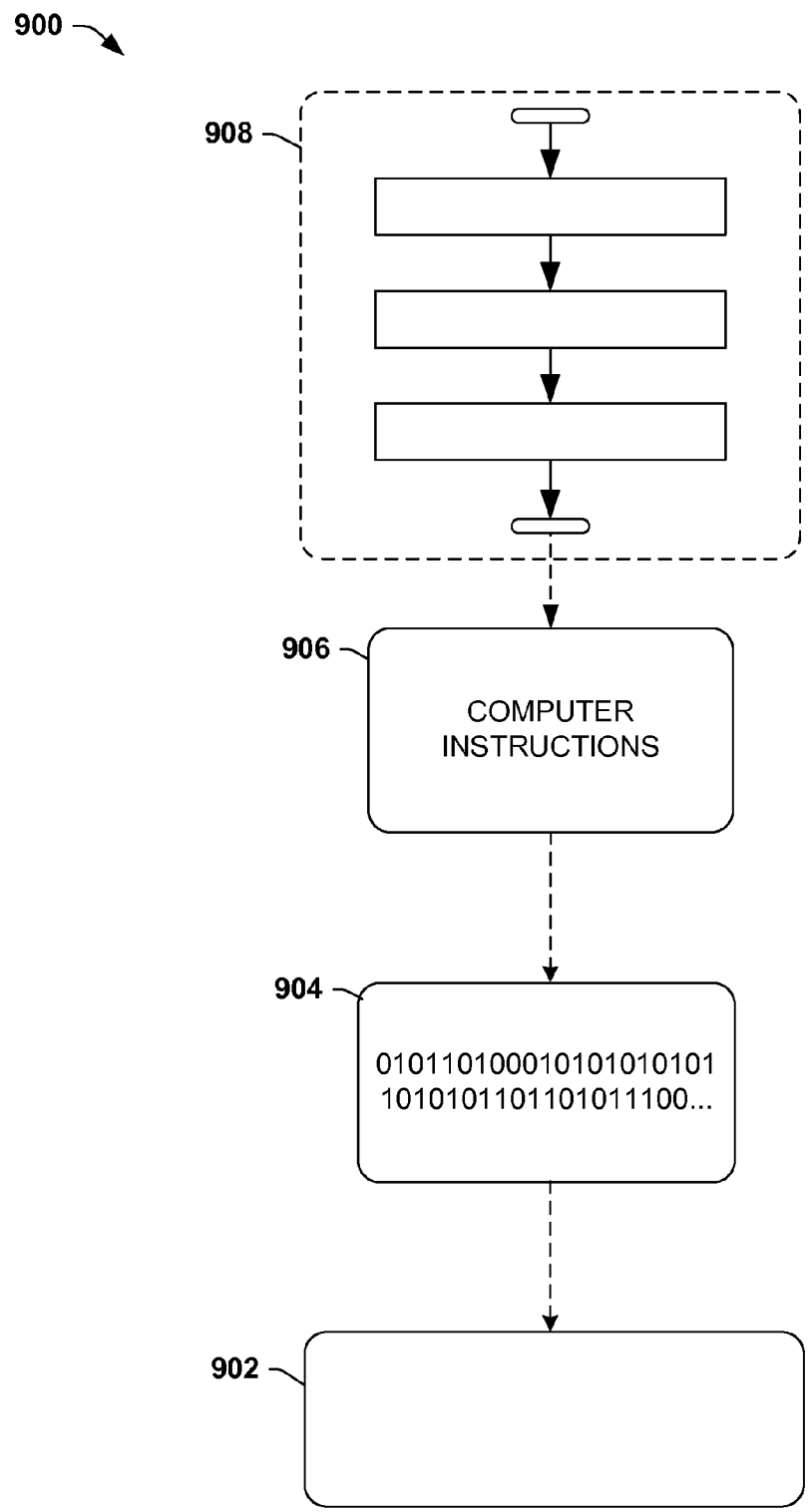
FIG. 9 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein (e.g., via a processing unit and/or memory). An example computer-readable medium that may be devised in these ways is illustrated in FIG. 9, wherein the implementation 900 comprises a computer-readable medium 902 (e.g., a CD-R, DVD-R, or a platter of a hard disk drive), on which is encoded computer-readable data 904. This computer-readable data 904 in turn comprises a set of computer instructions 906 configured to operate according to one or more of the principles set forth herein. In one such embodiment 900, the processor-executable instructions 906 may be configured to perform a method 908, such as at least some of the example method 700 of FIG. 7, for example. In another such embodiment, the processor-executable instructions 906 may be configured to implement a system, such as at least some of the exemplary environment 100 of FIG. 1, at least some of the exemplary system 200 of FIG. 2, at least some of the exemplary transmitter 300 of FIG. 3, and/or at least some of the exemplary receiver 400 of FIG. 4, for example. Many such computer-readable media may be devised by those of ordinary skill in the art that are configured to operate in accordance with one or more of the techniques presented herein.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A communication system for communicating information across a contactless data-link of a computed tomography (CT) system comprising a rotating member and a stationary member, comprising:

a transmitter configured to map digital data indicative of at least some of the information into a first analog signal, where mapping the digital data into the first analog signal comprises:
  selecting, from at least three possible signal configurations, a signal configuration corresponding to the digital data, where a first signal configuration of the three possible signal configurations specifies a first phase/frequency combination, a second signal configuration of the three possible signal configurations specifies a second phase/frequency combination, and a third signal configuration of the three possible signal configurations specifies a third phase/frequency combination, and
  generating the first analog signal according to the selected signal configuration;
the contactless data-link comprising a rotating portion operably coupled to the rotating member of the CT system and a stationary portion operably coupled to the stationary member of the CT system, the rotating portion separated from the stationary portion via an airgap, the contactless data-link configured to transfer the first analog signal from the transmitter to a receiver; and
the receiver configured to process the first analog signal to estimate the digital data mapped to the first analog signal.

2. The system of claim 1, the first analog signal representing at least 2 bits of data.

3. The system of claim 1, the receiver configured to estimate at least 2 bits of data from the processed first analog signal.

4. The system of claim 1, the receiver configured to estimate the digital data by:
comparing one or more characteristics of the first analog signal to respective characteristics of the at least three possible signal configurations to determine a matching signal configuration, and identifying a digital code word associated with the matching signal configuration.

5. The system of claim 1, the transmitter configured to:
receive the digital data encoded according to a first encoding scheme, and
encode the digital data according to a second encoding scheme to form a set of digital code words.

6. The system of claim 5, the transmitter configured:
map a first digital code word from the set of digital code words, corresponding to a first portion of the digital data, to generate the first analog signal according to the first signal configuration, and
map a second digital code word from the set of digital code words, corresponding to a second portion of the digital data, to generate a second analog signal according to the second signal configuration.

7. The system of claim 6, the first analog signal and the second analog signal sequentially transferred via the contactless data-link.

8. The system of claim 1, where the first signal configuration specifies a first phase and a first frequency and the second signal configuration specifies a second phase and a second frequency, the first phase different than the second phase and the first frequency different than the second frequency.

9. The system of claim 1, the digital data comprising image data yielded from detected radiation.

10. A method for communicating information between a rotating member and a stationary member of a computed tomography (CT) system, comprising:
selecting, from at least three possible signal configurations, a first signal configuration corresponding to a first digital code word indicative of at least some of the information to be transmitted between the rotating member and the stationary member, where the first signal configuration of the three possible signal configurations specifies a first phase/frequency/amplitude combination, a second signal configuration of the three possible signal configurations specifies a second phase/frequency/amplitude combination, and a third signal configuration of the three possible signal configurations specifies a third phase/frequency/amplitude combination;
generating a first analog signal according to the selected first signal configuration;
transmitting the first analog signal between the rotating member and the stationary member through an airgap separating the rotating member and the stationary member; and
processing the transmitted first analog signal to decode the first analog signal and estimate the first digital code word from the decoding.

11. The method of claim 10, comprising:
creating the at least three possible signal configurations.

12. The method of claim 10, comprising:
identifying possible digital code words comprised in a specified encoding scheme; and
mapping the identified digital code words to respective signal configurations of the at least three possible signal configurations.

13. The method of claim 10, the first analog signal representative of more than one bit of data.

14. The method of claim 10, comprising:
receiving digital data encoded according to a first encoding scheme; and
encoding the digital data according to a second encoding scheme to form a set of digital code words, the first digital code word comprised within the set of digital code words.

15. The method of claim 10, comprising:
selecting, from the at least three possible signal configurations, the second signal configuration corresponding to a second digital code word indicative of at least some of the information to be transmitted between the rotating member and the stationary member;
generating a second analog signal according to the selected second signal configuration;
transmitting the second analog signal between the rotating member and the stationary member; and
processing the transmitted second analog signal to decode the second analog signal and estimate the second digital code word from the decoding.

16. The method of claim 15, comprising:
compiling at least the estimate of the first digital code word and the estimate of the second digital code word to generate a communicated message; and
estimating an actual message intended to be transmitted between the rotating member and the stationary member based upon the communicated message.

17. The method of claim 10, where the first signal configuration specifies a first phase and a first frequency and the second signal configuration specifies a second phase and a second frequency, the first phase different than the second phase and the first frequency different than the second frequency.

18. A communication system for communicating information across a contactless data-link of a computed tomography (CT) system comprising a rotating member and a stationary member, comprising:

a transmitter configured to map digital data indicative of at least some of the information into an analog signal;

the contactless data-link comprising a rotating portion operably coupled to the rotating member of the CT system and a stationary portion operably coupled to the stationary member of the CT system, the rotating portion separated from the stationary portion via an airgap, the contactless data-link configured to transfer the analog signal from the transmitter to a receiver; and the receiver configured to process the analog signal to estimate the digital data mapped to the analog signal by:
  comparing one or more characteristics of the analog signal to at least three possible signal configurations to determine a matching signal configuration, where a first signal configuration of the three possible signal configurations specifies a first phase/frequency combination, a second signal configuration of the three possible signal configurations specifies a second phase/frequency combination, and a third signal configuration of the three possible signal configurations specifies a third phase/frequency combination, and
  identifying a digital code word associated with the matching signal configuration.

19. The system of claim 18, where the first signal configuration specifies a first phase and a first frequency and the second signal configuration specifies a second phase and a second frequency, the first phase different than the second phase and the first frequency different than the second frequency.

20. The system of claim 19, the digital data comprising image data yielded from detected radiation.

* * * * *